(12) United States Patent
Gupta et al.

(10) Patent No.: US 12,099,480 B1
(45) Date of Patent: Sep. 24, 2024

(54) AUTOMATED CLINICAL CONCEPT MAPPING USING SNOMED

(71) Applicant: IQVIA Inc., Danbury, CT (US)

(72) Inventors: Shaun Gupta, London (GB); Frederik B. C. Dieleman, London (GB); Daniel Homola, London (GB); Adam Webber, London (GB); Orla M. Doyle, London (GB); Nadejda Leavitt, Philadelphia, PA (US); John Rigg, London (GB); Patrick Long, Philadelphia, PA (US); Rabe'e Cheheltani, Danbury, CT (US)

(73) Assignee: IQVIA Inc., Durham, NC (US)

( * ) Notice: Subject to any disclaimer, the term of this patent is extended or adjusted under 35 U.S.C. 154(b) by 173 days.

(21) Appl. No.: 16/800,873

(22) Filed: Feb. 25, 2020

Related U.S. Application Data

(60) Provisional application No. 62/899,436, filed on Sep. 12, 2019.

(51) Int. Cl.
*G06F 16/21* (2019.01)
*G06F 16/215* (2019.01)
(Continued)

(52) U.S. Cl.
CPC .......... *G06F 16/211* (2019.01); *G06F 16/215* (2019.01); *G06F 16/9024* (2019.01); *G16H 70/60* (2018.01); *G06N 3/04* (2013.01)

(58) Field of Classification Search
CPC ................................ G16H 70/60; G06N 3/04
(Continued)

(56) References Cited

U.S. PATENT DOCUMENTS

2004/0049522 A1* 3/2004 Streepy, Jr. ............. G16H 70/60
2008/0201280 A1* 8/2008 Martin .................... G06N 20/00
706/12
(Continued)

FOREIGN PATENT DOCUMENTS

WO WO-2017172629 A1 * 10/2017 ........... G06K 9/6277
WO WO-2019191559 A1 * 10/2019 ........... G06K 9/6215

OTHER PUBLICATIONS

CDC; International Classication of Diseases, (ICD-10-CM/PCS) Transition—Background; National Center for Health Statistics; https://www.cdc.gov/nchs/icd/icd10cm_pcs_background.htm (Year: 2015).*

(Continued)

*Primary Examiner* — Hiep V Nguyen
(74) *Attorney, Agent, or Firm* — John Maldjian, Esq.; David L. D'Amato, Esq.; Stevens & Lee PC

(57) ABSTRACT

A graph-based clinical concept mapping algorithm maps ICD-9 (International Classification of Disease, Revision 9) and ICD-10 (International Classification of Disease, Revision 10) codes to unified Systematized Nomenclature of Medicine (SNOMED) clinical concepts to normalize longitudinal healthcare data to thereby improve tracking and the use of such data for research and commercial purposes. The graph-based clinical concept mapping algorithm advantageously combines a novel graph-based search algorithm and natural language processing to map orphan ICD codes (those without equivalents across codebases) by finding optimally relevant shared SNOMED concepts. The graph-based clinical concept mapping algorithm is further advantageously utilized to group ICD-9/10 codes into higher order, more prevalent SNOMED concepts to support clinical interpretation.

24 Claims, 18 Drawing Sheets

(51) Int. Cl.
  *G06F 16/901* (2019.01)
  *G06N 3/04* (2023.01)
  *G16H 70/60* (2018.01)
(58) Field of Classification Search
  USPC .......................................................... 705/2
  See application file for complete search history.

(56) References Cited

U.S. PATENT DOCUMENTS

| | | | | |
|---|---|---|---|---|
| 2011/0301982 | A1* | 12/2011 | Green, Jr. | G06Q 10/06 |
| | | | | 705/3 |
| 2012/0110016 | A1* | 5/2012 | Phillips | G06F 16/285 |
| | | | | 707/E17.014 |
| 2012/0197657 | A1* | 8/2012 | Prodanovic | G16H 40/20 |
| | | | | 705/2 |
| 2013/0185094 | A1* | 7/2013 | Mukerji | G06Q 10/00 |
| | | | | 705/3 |
| 2014/0372140 | A1* | 12/2014 | Reddy | G06F 8/30 |
| | | | | 705/2 |
| 2015/0356647 | A1* | 12/2015 | Reiser | G06Q 30/04 |
| | | | | 705/3 |

OTHER PUBLICATIONS

Xu, Junchuan; Mapping Snomed CT to ICD-10-CM; Rutgers The State University of New Jersey, School of Health Related Professions. ProQuest Dissertations Publishing, 2016. 10103053 (Year: 2016).*

* cited by examiner

FIG 8

| Column name | Contents |
|---|---|
| concept_id | OMOP* concept id<br><br>*Observational Medical Outcomes Partnership |
| concept_name | Concept name |
| domain_id | Domain of concept (e.g. Observation/Drug/Device/Route etc). |
| vocabulary_id | Vocabulary of concept – SNOMED/ICD-9/ICD-10 |
| concept_class_id | Denotes concept class (e.g. Substance/11-digit NDC/Cost etc.) |
| concept_code | Code of concept |

Table 1

FIG 9

| Column name | Contents |
|---|---|
| concept_id_1 | OMOP concept id for first concept |
| concept_id_2 | OMOP concept id for second concept |
| relationship_id | Relationship type (e.g. "Maps to", "Has method", etc.) – we are only interested in "Maps to" and "Mapped from" relationships. |

Table 2

FIG 10

| Column name | Contents |
|---|---|
| snomed | SNOMED code |
| icd10 | ICD-10 code |
| icd9 | ICD-9 code |
| desc_10 | Text description of ICD-10 code |
| desc_9 | Text description of ICD-9 code |
| cnt_10 | Count of claims billed to the ICD-10 code |
| cnt_9 | Count of claims billed to the ICD-9 code |

Table 3

*FIG 11*

| Column name | Contents |
|---|---|
| ancestor_concept_id | Ancestor SNOMED concept id |
| descendant_concept_id | Descendent SNOMED concept id |
| min_levels_of_separation | Minimum level of separation between nodes |
| max_levels_of_separation | Maximum level of separation between nodes |

Table 4

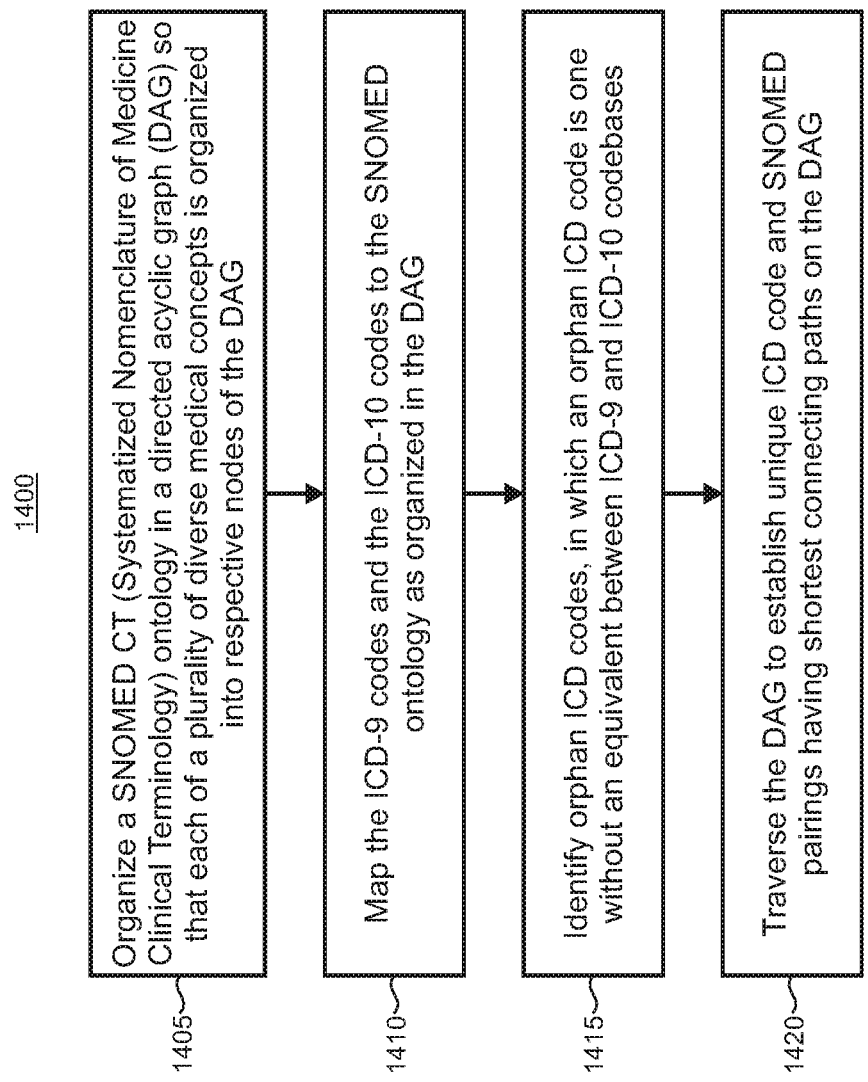

1505 → Obtain mappings between ICD (International Classification of Disease) codebases and a SNOMED CT ontology that is organized as a directed acyclic graph (DAG), in which the ICD codebases are published as a series of revisions and at least include one previous revision and one subsequent revision 1510 → Use the mappings to identify orphan ICD codes without equivalents across the codebases 1515 → Traverse the DAG to pair the identified orphan ICD codes using using codes from a previous ICD codebase revision as queries and codes from a subsequent ICD codebase revision as targets 1520 → Repeat the DAG traversal using codes from a subsequent ICD codebase revision as queries and codes from a previous ICD codebase revision as targets and merge the successive results of 1525 → Reduce paired orphan ICD codes by removing duplicates or by keeping pairs that fall within a predetermined distance on the DAG

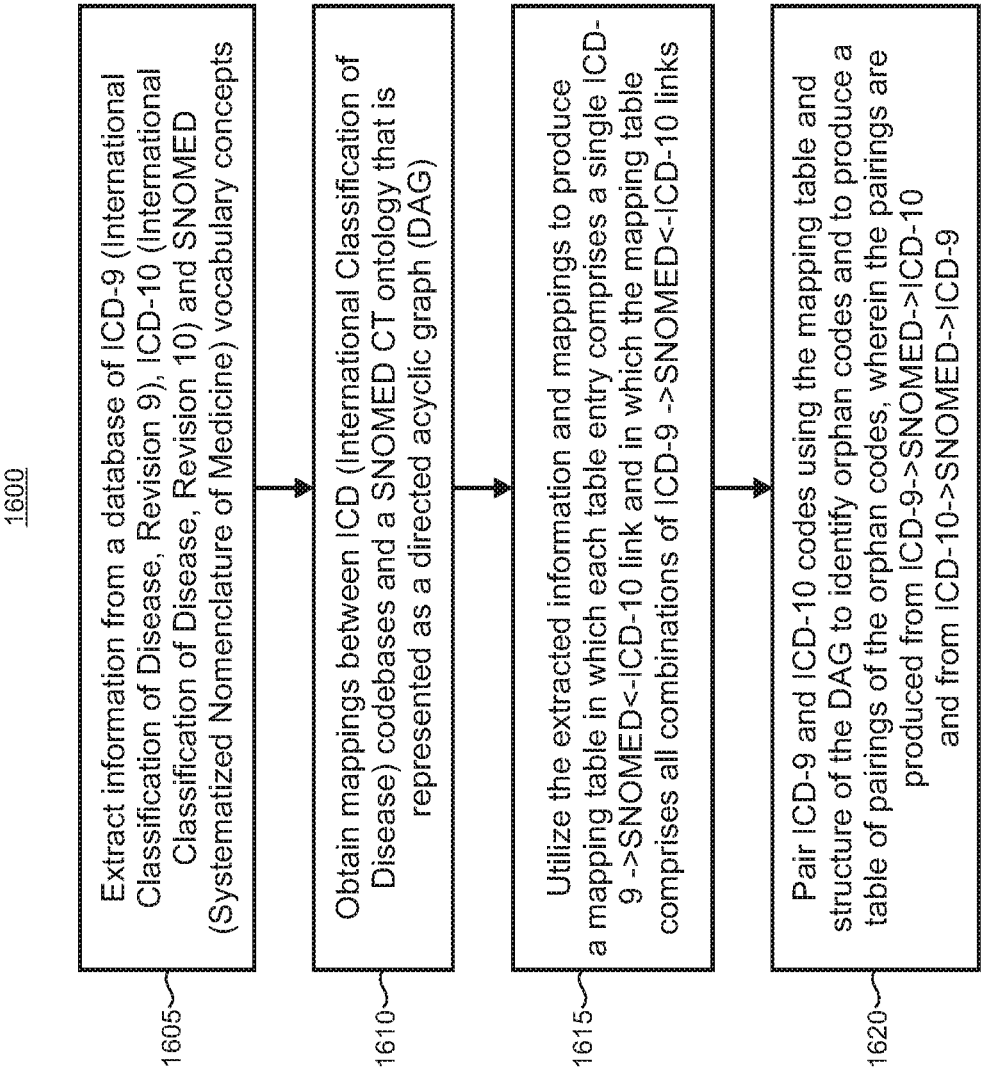

AUTOMATED CLINICAL CONCEPT MAPPING USING SNOMED

CROSS-REFERENCE TO RELATED APPLICATION

This application claims benefit and priority to U.S. Provisional Application Ser. No. 62/899,436 filed Sep. 12, 2019, entitled "Automated Clinical Concept Mapping using SNOMED" which is incorporated herein by reference in its entirety.

BACKGROUND

SNOMED CT (Systematized Nomenclature of Medicine—Clinical Terminology, herein simply referred to as SNOMED) is a systematic, computer-processable collection of medical terms, in human and veterinary medicine, to provide codes, terms, synonyms and definitions which cover anatomy, diseases, findings, procedures, microorganisms, substances, etc. It allows a consistent way to index, store, retrieve, and aggregate medical data across specialties and sites of care.

In October 2015 the United States switched from the International Classification of Disease, Revision 9 (ICD-9) to the ICD-10 codebase to bill claims of diagnoses. There are few clear one-to-one mappings between ICD-9 and ICD-10 codes. Rather, most mappings are incomplete between the two codebases. The absence of a readily available, clinically relevant, and interpretable mapping of ICD-9 to ICD-10 poses challenges when tracking medical history for a cohort of patients across many years.

SNOMED was developed as a unified clinical concept ontology to facilitate the interoperability between electronic healthcare systems and to support clinical research using electronic medical record data. Both ICD-9 and ICD-10 codes may be mapped to SNOMED concepts and in many cases ICD-9 and 10 codes map to shared SNOMED concepts (i.e., concepts that contain both ICD-9s and ICD-10s). However, around seven thousand of the 15 thousand ICD-9 and 44 thousand of the 110 thousand ICD-10 codes do not map to shared SNOMED codes. These codes are referred to as orphans. Orphans limit ICD codebase interoperability because they prevent direct linking of ICD-9 and ICD-10 codes via a shared SNOMED concept.

SUMMARY

A graph-based clinical concept mapping algorithm maps codes from different ICD codebases, for example ICD-9 and ICD-10, to unified SNOMED clinical concepts to normalize longitudinal healthcare data to thereby improve tracking and the use of such data for research and commercial purposes. The graph-based clinical concept mapping algorithm advantageously combines a novel graph-based search algorithm and natural language processing to map orphan ICD codes (those without equivalents across codebases) by finding optimally relevant shared SNOMED concepts. The graph-based clinical concept mapping algorithm is further advantageously utilized to group ICD-9 and ICD-10 codes into higher order, more prevalent SNOMED concepts to support clinical interpretation.

In an illustrative example, the present graph-based clinical concept mapping algorithm automates the process of ICD-9 to ICD-10 mapping by leveraging the SNOMED clinical ontology and selecting optimal mappings in cases of orphan ICD codes. Additionally, it can search for higher order ICD code groupings within SNOMED to support the codebase interpretability. Accordingly, the present graph-based clinical concept mapping algorithm improves the interoperability between ICD-9 and ICD-10 codebases, which positively impacts any commercial or research endeavor leveraging longitudinal diagnostic claims data.

Longitudinal diagnostic claims data may be of value to machine learning efforts that use patient medical history to predict future medical events, such as diagnoses, changes in line therapy, or responsiveness to treatments. Leveraging both ICD-9 and ICD-10 claims data through SNOMED mapping increases both the number of eligible patients and the length of patient medical histories available to train machine learning algorithms, which supports the development of more statistically robust and performant predictive models. For example, the present graph-based clinical concept mapping algorithm can be used to train machine learning models with equivalent performance to those trained on clinical features curated by domain experts.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings.

DESCRIPTION OF THE DRAWINGS

FIGS. 8-11 show illustrative tables of information that may be utilized in an illustrative software-based algorithm for implementing the present graph-based automated clinical concept mapping using SNOMED;

FIGS. 14-16 are flowcharts of illustrative methods performed by a computing device to implement the present graph-based clinical concept mapping algorithm;

Like reference numerals indicate like elements in the drawings. Elements are not drawn to scale unless otherwise indicated.

DETAILED DESCRIPTION

The current state of the art relies on a combination of human clinical expertise and bridge files that map ICD-9 to ICD-10 equivalents using general equivalence mapping (GEM) systems. GEMs are designed to support all uses of coded data, and for ease of use, the system is bidirectional, which means it can be used to translate from ICD-9 to ICD-10 (forward mapping) and from ICD-10 to ICD-9 (backward mapping). This bidirectional feature enables coding professionals to check their work to ensure the best possible match. However, GEM systems do not fully capture the complex relationships present between the ICD-9 and the ICD-10 which do not support a one-to-one mapping between the codebases. Because the ICD-10 system comprises many more codes than ICD-9, many ICD-9 codes will map to more than one ICD-10 code. In some cases, an ICD-9 code will not have a match in ICD-10. Likewise, some ICD-10 codes represent new concepts for which there is no ICD-9 code. More than one ICD-9 code may be needed to completely and correctly understand the ICD-10 correlative. Similarly, for any given ICD-10, there may be more than one possible ICD-9 translation.

Accordingly, GEMs may have limited utility as only 24% of ICD-9 codes and 5% of ICD-10 codes have one-to-one mapping to the other codebase, 3% and 1% respectively fail to match, and the remaining codes have one or more approximate matches. To address this shortcoming, domain experts manually group ICD-9 and ICD-10 codes into meaningful predictors which can be expensive and time-consuming. In addition, such manual solutions are not able to determine in advance what ICD-9 and ICD-10 groupings are well represented in each population.

Figure 1:
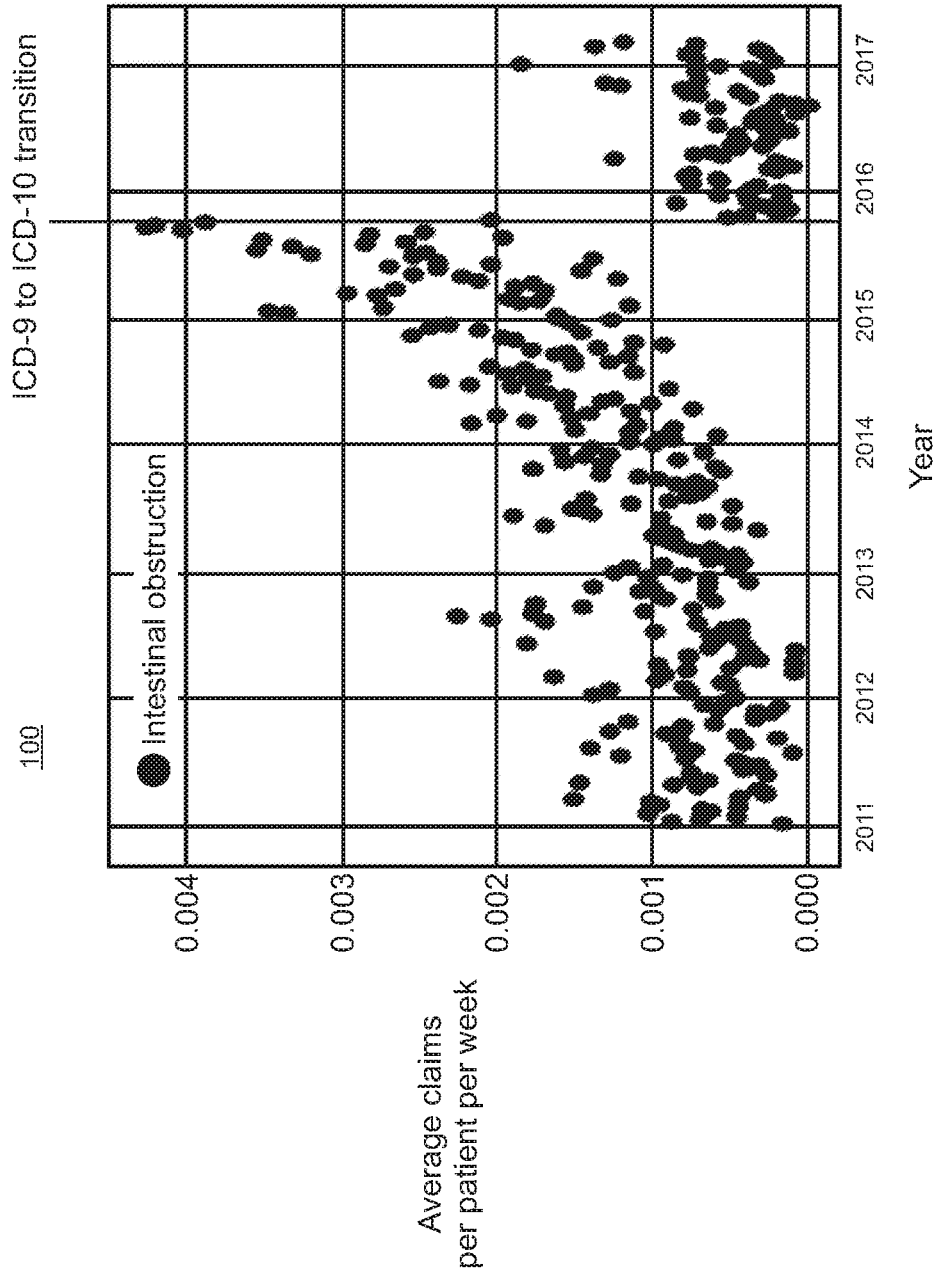
FIG. 1 is a graph of average number of claims per patient per week over the ICD transition period for manually clinically coded data.

For example, as shown in FIG. 1, a graph 100 of manually clinically coded data for an average number of claims per patient for week shows a severe mismatch over the ICD transition period. Discontinuity of the claims across the ICD transition period points to an unsuccessful conceptual mapping of ICD-9 and ICD-10 features if one assumes the underlying medical diagnoses across that period stayed stable.

In an analysis of the most prevalent SNOMED concepts, 30% were considered to have discontinuous transitions. The clinical mapping performed by experts (93 clinical concepts) still demonstrated around 10% of these discontinuous transitions. Such discontinuous transitions are an artifact of target ICD codes not being present in the positive/control cohort, resulting in SNOMED concepts being linked to mainly or only one ICD code version—something that could be improved by prioritizing pairs with high ICD code prevalence from the cohort of interest during the reduction phase of the algorithm.

Conventional mapping of orphan ICD codes across codebases and the rollup of multiple ICD codes into higher level clinical categories currently rely on the judgement of clinical/domain experts in combination with established ICD hierarchies. The ICD system includes standard hierarchy designed for billing purposes. This hierarchy may be used to aggregate granular ICD codes into more interpretable rollups (e.g., ICD Level 4 is a higher-level aggregation and is very interpretable).

However, the ICD codebase presents key challenges in automated mapping scenarios including those, for example, that utilize machine learning for event prediction. As it was built for medical billing, the ICD codebase may miss the intricacies and complexities of medical diagnostics. While SNOMED was built to resolve this challenge, it is not obvious which level of SNOMED concepts should be used to conduct research (overall and with the specific use case of machine learning), and whether clinically relevant SNOMED hierarchies vary by disease and by variable within a disease.

In the following illustrative example, mapping from ICD-9 to ICD-10 codebases is discussed in detail. However, it is emphasized that the principles taught in the illustrative example are not restricted to ICD-9 and ICD-10 codebases, and may be expected to applicable to other future revisions of ICD, such as ICD-11, etc., to thereby provide substantially all of the attendant benefits and advantages automated clinical concept mapping using SNOMED discussed below.

There is also no easy solution for mapping ICD-9 to ICD-10. While an ICD-9 to ICD-10 mapping file exists, it is not ideal since ICD-9 to ICD-10 is not one-to-one but rather a one-to-many relationship and its use requires expert clinical supervision. SNOMED concepts can be mapped to ICD-9 and ICD-10 and mapping files exist for this purpose, but the presence of orphans prevents a complete mapping via SNOMED. Additionally, while SNOMED can provide an opportunity for higher order aggregations of concepts, there are no automated methods for doing so that consider the prevalence of codes within a cohort of interest. The present graph-based clinical concept mapping algorithm solves such challenges presented by the ICD codebase.

Figure 2:
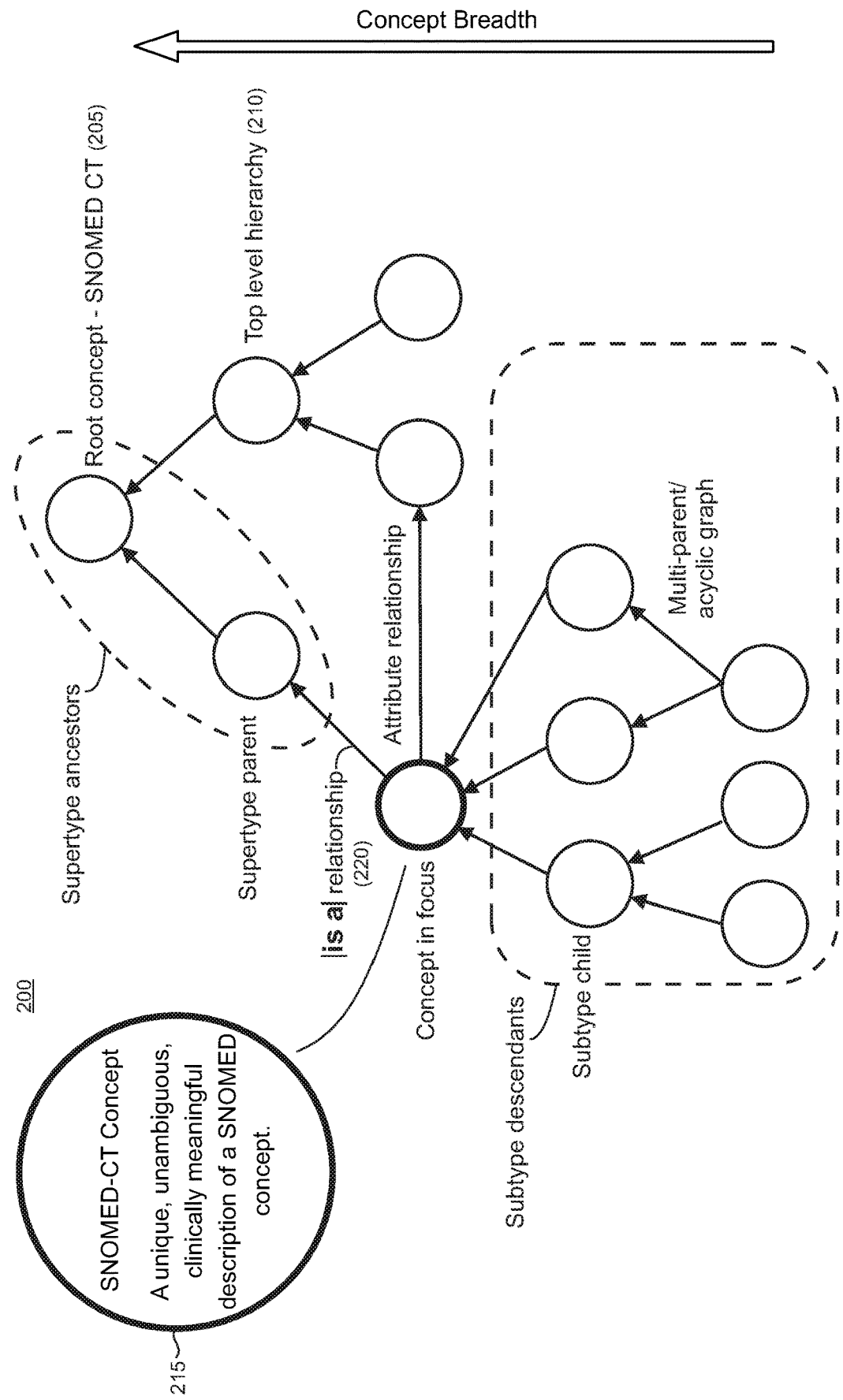
FIG. 2 shows an illustrative directed acyclic graph (DAG) and a SNOMED concept/DAG node.

FIG. 2 shows an illustrative generalized directed acyclic graph (DAG) 200 that provides an organization for a universal SNOMED-CT clinical concept ontology that uses a subtype classification system to enable aggregation of information for statistical analysis based on a hierarchy of types. The DAG comprises a set of nodes connected to one another by lines (edges) in which each connection has a specified direction such that no route that follows the direction of the connections enters a loop (cycle). SNOMED CT concepts are nodes in the DAG and subtype relationships are the directed lines that connect them. All subtype relationships lead from a more specific concept to a more general concept, so a cycle would be a logical error. For example, if "rubella virus" is a type of "virus" and "virus" is a type of "microorganism", then "microorganism" cannot be a type of "rubella virus."

The top of the SNOMED CT hierarchy is occupied by the root concept (|SNOMED CT concept|) (as indicated by reference numeral 205). All concepts are descended from this root concept through at least one sequence of |is a| relationships. This means that the root concept is a supertype of all other concepts and all other concepts are subtypes of the root concept. Each node, (representatively indicated by reference numeral 215), is a clinically defined SNOMED CT concept and the DAG 200 thus captures the hierarchies and relationships among the concepts. Concepts with the most general meanings are presented at the top of the hierarchy, with the concepts linked to them at the level beneath, and so on.

The direct subtypes of the root concept are referred to as "top-level concepts" in top level hierarchy 210. These concepts are used to name the main branches of the hierarchy. Each of these top-level concepts, together with their many subtype descendants, forms a major branch of the SNOMED CT hierarchy and contains similar types of concepts. As the hierarchies descend (that is, more |is a| relationships are added below the top-level concepts), the meanings of the concepts are increasingly more specific or specialized.

Figure 3:
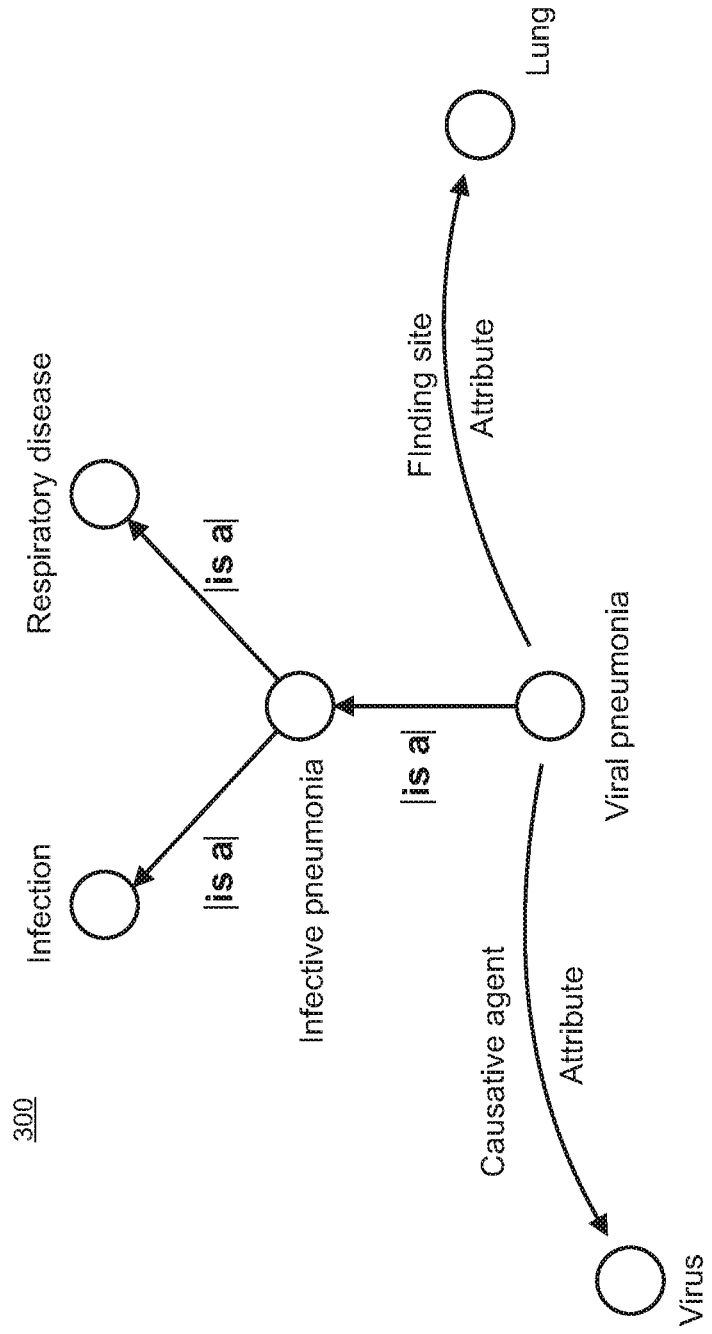
FIG. 3 shows illustrative examples of relationships and attribute relationships.

A relationship represents an association between two concepts. Relationships are used to logically define the meaning of a concept in a way that can be processed by a computer. A third concept, called a relationship type (or attribute), is used to represent the meaning of the association between the source and destination concepts. There are different types of relationships available within SNOMED. Concepts have at least one |is a| clinically meaningful relationship 220 to another concept, along with one or more attribute relationships defining various links, for example, "finding site" of a disease or a "causative agent," as illustratively shown in DAG 300 in FIG. 3. An attribute relationship contributes to the definition of the source concept by associating it with the value of a defining characteristic. The characteristic (attribute) is specified by the relationship type and the value is provided by the destination of the relationship.

Subtype relationships are the most widely used type of relationship. Subtype relationships use the |is a| relationship type and are therefore also known as |is a| relationships. Almost all active SNOMED CT concepts are the source of at least one |is a| relationship. The only exception is the root concept |SNOMED CT Concept| which is the most general concept. The |is a| relationship states that the source concept is a subtype of the destination concept. SNOMED CT relationships are directional and the |is a| relationship read in the reverse direction states that the destination concept is a supertype of the source concept.

The |is a| relationships form the hierarchies of SNOMED CT. The source concept of the |is a| relationship has a more specific clinical meaning than the target concept. This means that the level of clinical detail of the concepts increases with the depth of the hierarchies.

If two concepts are directly linked by a single |is a| relationship, the source concept is said to be a "subtype child" of the destination concept. The destination concept is referred to as a "supertype parent." Any concept that is the source of a sequence of one or more |is a| relationships leading to a specified destination concept, is a "subtype descendant" of that concept. Similarly, any concept that is the destination of a sequence of one or more |is a| relationships leading to a specified source concept, is a "supertype ancestor" of that concept. It is also said that the source concept of a relationship "is subsumed by" the target concept, and that the target concept of a relationship "subsumes" the source concept.

Each concept can have relationships to several other concepts (i.e. a concept may have multiple supertype parent concepts). As a result, the SNOMED CT hierarchy is not a simple tree but has a structure that is known as a "polyhierarchy."

Figure 4:
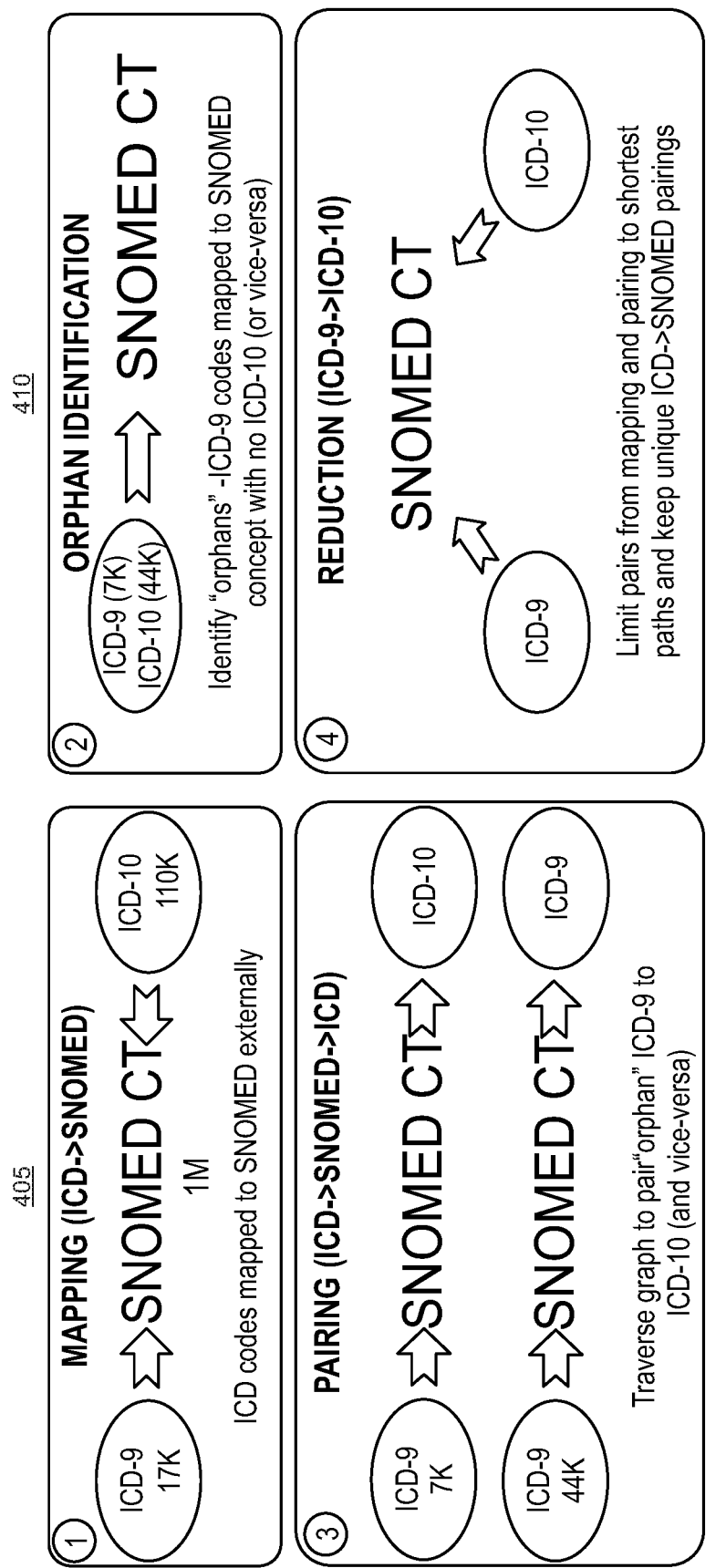
FIG. 4 shows illustrative ICD-9 to ICD-10 mapping in four stages.

The ICD-SNOMED concept mapping is now presented. The DAG structure of SNOMED performs two functions: (i) provides a mapping between ICD-9 and ICD-10 and (ii) for any graph/tree-based ontology, a custom rollup algorithm groups together codes/concepts into higher level, more easily interpretable features. The ICD-9 and ICD-10 mappings are generated via four stages, as shown in FIG. 4:

(1) obtain external ICD-SNOMED mappings (indicated by reference numeral 405);
(2) identify orphan ICD codes (ICD codes without equivalents across codebases) (410);
(3) pair orphan ICD codes (415); and
(4) create subsets of identified pairs to those closest on the SNOMED graph (420). A pre-built Word2Vec two-layer neural network model may be optionally utilized to find the ICD code pair having the highest semantic similarity.

For example, after steps (1) and (2), to find ICD-10 pairs for orphan ICD-9 codes (those without ICD-10 equivalents), starting from SNOMED nodes mapped to the ICD-9 query of interest, the SNOMED DAG is traversed until a SNOMED concept is found that has ICD-10 code(s) mapped to it. Then during the reduction step (4), if multiple codes are equidistant from the ICD-9 query code, the algorithm has the option to look at the clinical descriptions of these target ICD-10 codes and use a pre-built Word2Vec model to find the one with the highest semantic similarity.

To protect against an overly exhaustive graph traversal that could find pairings far from the original concept, the mapping approach fixes the search radius to a predetermined number of nodes (e.g., five) and will search the graph up and down within this limit. If a corresponding ICD-10 is not found (for an ICD-9 query), no mapping occurs. This limit is to prevent completely irrelevant pairings, or pairings that go to the root of the graph.

The search itself is performed using both ICD-9 and ICD-10 as the query, resulting in two sets of mappings. These are then combined, at which point duplicates are removed, and only pairs closest on the SNOMED graph are kept.

Figure 5:
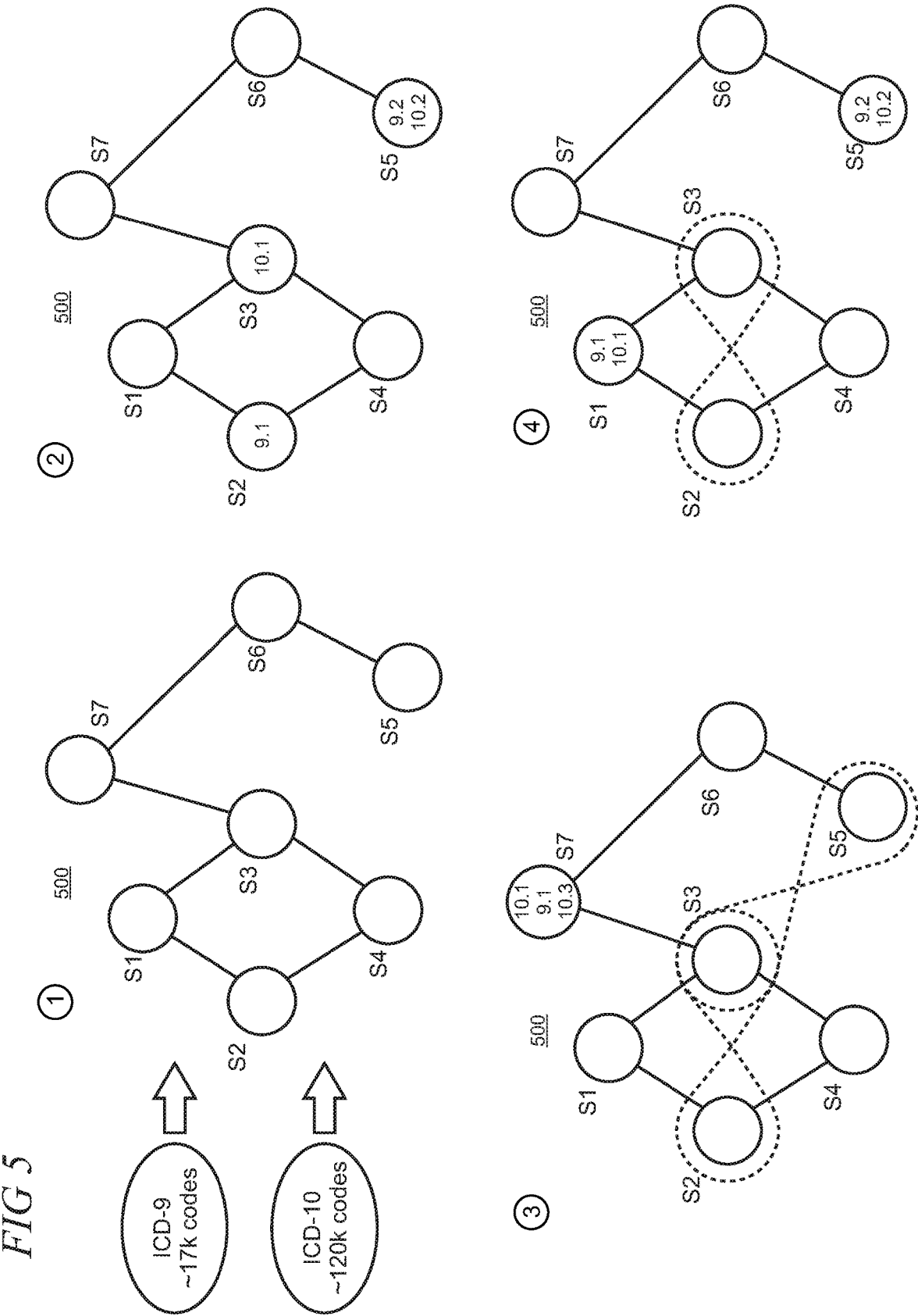
FIG. 5 shows illustrative resolution of orphan codes using SNOMED DAG traversal.

FIG. 5 shows an illustrative example of ICD-SNOMED concept mapping using a DAG 500 in which SNOMED concepts are labelled as SX, ICD-9 codes as 9.X and ICD-10 codes as 10.X. Ancestors are positioned higher on the DAG and descendants are positioned lower. The four steps applied to this illustrative example are: (1) ICD to SNOMED mapping. (2) Orphan identification: S2 and S3 contain orphan codes (9.1 and 10.1 respectively), while S5 contains both an ICD-9 and an ICD-10 code. (3) Pairing: The orphan codes in S2 and S3 can be paired together in their common ancestor S1. The orphan code in S3 can also be paired with the non-orphan codes in S5 into their common ancestor S7. (4) Reduction: Only the pairing of S2 and S3 into Sb is kept since the distance between them is smaller than the distance between S3 and S5.

The code for the full mapping algorithm operates as follows:
1. Mapping—ICD-SNOMED mappings are obtained from external sources and pre-processed.
2. Orphan Identification (setting query and targets):
    a. Define query and target—ICD 9 and ICD 10 from input ICD-SNOMED mappings
    b. Identify query SNOMED nodes with no directly associated target i.e., orphans
    c. Identify all possible SNOMED targets (i.e., orphan SNOMED nodes linked to one ICD version with no query, and all nodes which already have an ICD 9→ICD-10 pairing)
3. Pairing:
    a. For queries, identify all ancestors in SNOMED graph
    b. Define ancestor to be pivot node
    c. For all target nodes, identify all possible ancestors within (optional) minimum separation distance
    d. Identify target node ancestors that are pivots to queries—queries linked to targets via these pivots e. Search is done in reverse direction (i.e., linking to pivots lower down in graph as opposed to up)
f. Resultant pivot nodes become SNOMED concepts that group together orphan queries and corresponding targets.
4. Repeat steps 2 and 3 with query and target reversed (i.e., if first run was with ICD-9 as query and ICD-10 as target, second run will be with ICD-10 as query and ICD-9 as target) and merge together outputs.
5. Reduction:
   a. Remove duplicate pairs
   b. Sub-select pairs closest together on SNOMED graph
   c. Optional: look at the clinical descriptions of the paired query and target codes and use a pre-built Word2Vec model to find the one with the highest semantic similarity.

As noted above, during the reduction step, a Word2Vec two-layer neural network model may be optionally used to sub-select optimal SNOMED concepts in the situation where two or more target nodes are found equidistant with the shortest path of all targets to the query node. In this case, their descriptions and claim counts are used to choose between them. First, ICD target descriptions with the largest combined total of claim counts are selected for each SNOMED target node. Then the node with the semantically most similar (using cosine similarity) target description is selected.

Figure 6:
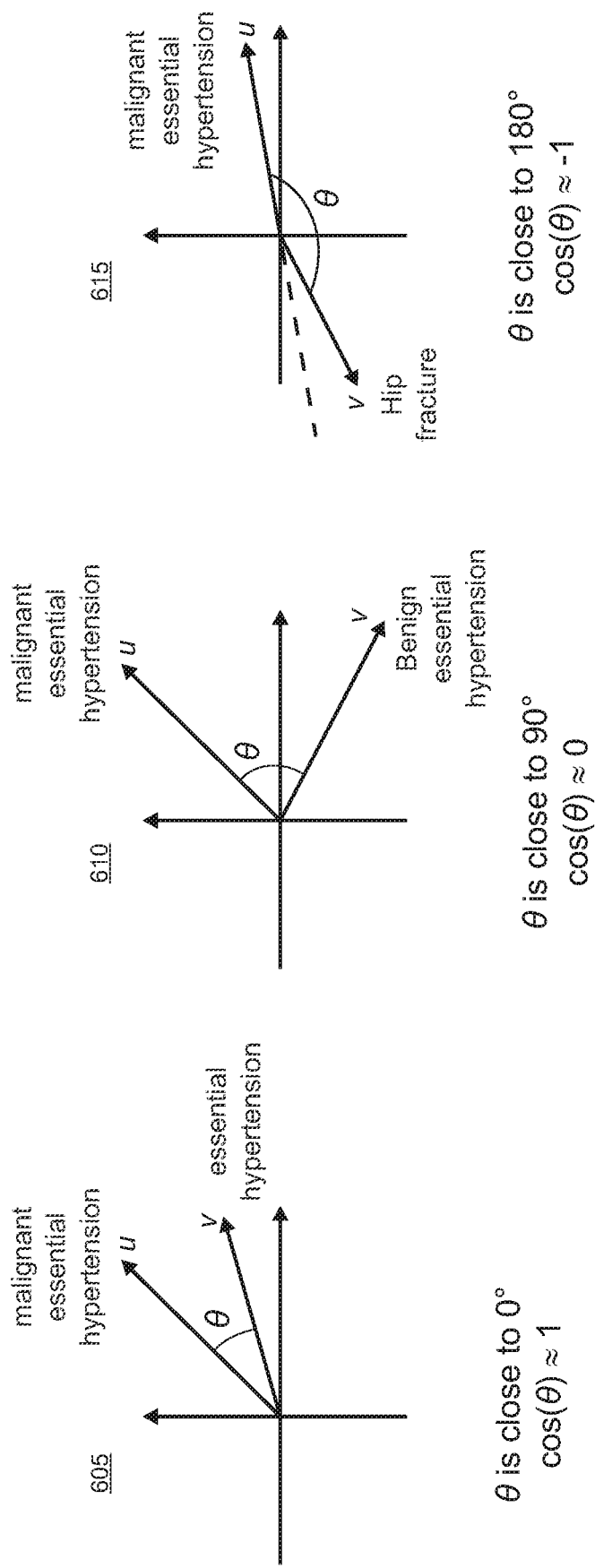
FIG. 6 shows illustrative resolution of tied ICD pairings by comparing semantic similarity between ICD code descriptions.

FIG. 6 shows an illustrative example of the application of semantic similarity between ICD code descriptions using cosine similarity in which two non-zero vectors u and v are utilized to represent ICD code descriptions. Two code description vectors with the same orientation have a cosine similarity of 1, two vectors oriented at 90° relative to each other have a similarity of 0, and two vectors diametrically opposed have a similarity of −1, independent of their magnitude. As shown in the first set of axes 605, the angle θ between the code description vectors is close to zero which implies that their cosine similarity will be close to 1. As the code descriptions become more dissimilar, the angle θ increases and cosine similarity will take a smaller value, as shown on the second set of axes 610. The vectors may represent diametrically opposed concepts as the angle θ approaches 1800 as shown on the third set of axes 615.

Evaluation of semantic similarity may be implemented using a two-layer neural network model. For example, a pre-trained Word2Vec model may be obtained by training a Continuous Bag of Words (CBOW) Word2Vec algorithm on ICD code descriptions for five epochs, with a vector dimension of 300, window of eight, minimum word occurrence threshold of three, down sampling threshold of 0.001, and minimum learning rate of 0.0001. The sum of the context vectors is used as the CBOW mean. Negative sampling is applied, with five noise words drawn and a negative sampling exponent of 0.75. During application of the Word2Vec model on an ICD description, the Term Frequency Inverse Document Frequency (TFIDF) weighted average of word vectors in the description sentence is used to create an embedding vector for the description.

The SNOMED Concept Rollup Algorithm is now presented. At the completion of the mapping process, all ICD-9 and ICD-10 code are mapped to a SNOMED concept that contains multiple ICD-9 and ICD-10 codes, resulting in a rudimentary aggregation (rolling up) of multiple ICD codes into a single SNOMED concept. However, to allow for even more aggregation of features, additional rolling up functionality was added to this algorithm, which allows SNOMED codes to be aggregated using the SNOMED DAG. Since the SNOMED DAG is based on medical knowledge, to some extent this process automatically emulates what a clinical coder would do in a clinically driven feature creation process.

The rollup algorithm has two components—One for creating individual SNOMED nodes that contain several ICD (or other) codes and another for defining a network of these nodes. This network object implements many methods for manipulating individual and groups of nodes on this graph and to systematically roll them up.

Note that only the ICD codes present in the input feature flag table are used for mapping/rollup i.e., if there's an ICD-9 code but it's corresponding ICD-10 code(s) is not present in the flag table, i.e., it's not in the patient cohort from which the ICD-9 or 10 codes were identified, SNOMED will not pull it in automatically.

Figure 7:
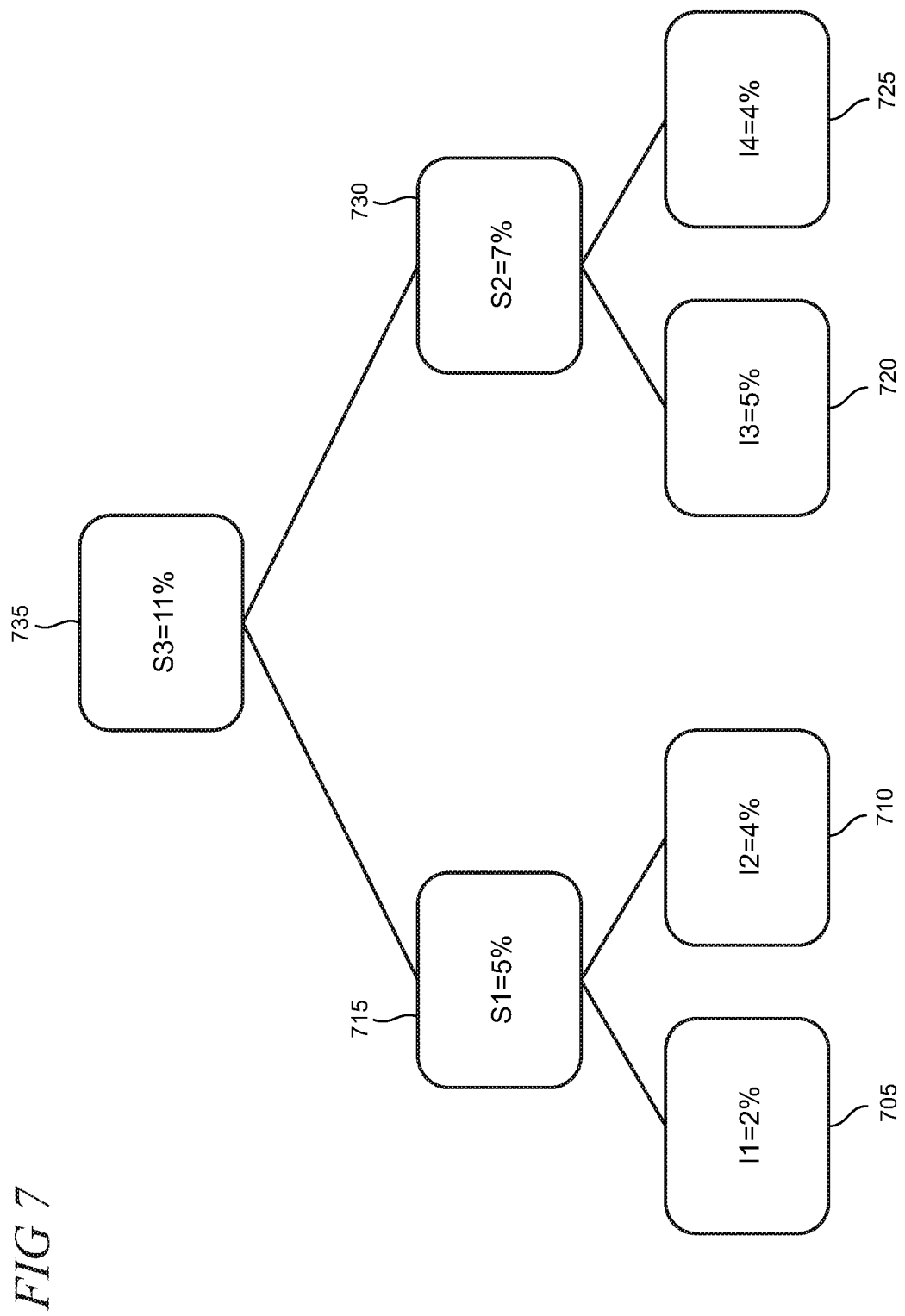
FIG. 7 shows an illustrative SNOMED concept rollup.

SNOMED concepts may be desired to be present in at least 10% of patients, as illustratively shown in FIG. 7. I1 and I2 ICD codes (as respectively indicated by reference numerals 705 and 710) were mapped to the same SNOMED code S1 (as indicated by reference numeral 715). However, they are missing in 95% of the patients, i.e., present in only 5%. Fortunately, there is another SNOMED code adjacent to S1 on the SNOMED DAG (and thus clinically similar), which contains I3 and I4 ICD codes (as respectively indicated by reference numerals 720 and 725). In fact, S1 and S2 (as indicated by reference numeral 730) are so close to each other in the SNOMED DAG that they can be rolled up into the parent node. Therefore, S3 (as indicated by reference numeral 735) is defined which now will contain I1, I2, I3, and I4. Together, these four ICD codes are now present in 11% of patients so S3 is kept as a feature for modeling.

There are three optional strategies that may be utilized:
1. Non-redundant: Each code is rolled up that is below the threshold until they end up in a SNOMED code that is above the threshold. The rolled-up SNOMED codes are deleted, i.e., the above example ends up with S3 and deletes S1 and S2. Importantly however, if S1 were above 10%, then only S2 is rolled up into S3 and ends up with S1 and S3.
2. Redundant-keep: The above example is modified slightly with S1>10% but S2<10%. Since these nodes are siblings on the network (i.e., connected by a parent) both nodes are rolled up into S3 even though S1 was above the threshold on its own. Note that only S2 is deleted. Thus, S3>10% containing I1, I2, I3, and I4, but S1 is kept which will have I1 and I2 codes. Because of this, the two resulting features are slightly correlated.
3. Redundant-delete: Same as redundant-keep, but both S1 and S2 are deleted even though S1 was above 10% on its own.

Details of an illustrative use case are now presented. The present graph-based algorithm facilitates the use of patient ICD claims data that span ICD revisions for longitudinal analysis of patient medical history. Enhanced ICD interoperability may be used to improve patient journey analysis, healthcare delivery optimization, and predictive modeling/machine learning offerings. Limited availability of patient medical data is a hinderance to predictive modeling, especially for rare diseases, which suffer from low patient prevalence and therefore limited data for model training. Practical use cases for machine learning enabled by the present graph-based algorithm include:
1. The use of longer patient histories for model training i.e., one can more easily and effectively leverage patient ICD claims data that span the ICD-10 transition.

2. Automated ICD mapping supports generation of stable features for model training and hence better model performance.
3. Automated feature rollup helps generate interpretable clinical features for predictive modeling. Interpretable features are often necessary for stakeholder buy-in when deploying a model in a commercial or clinical setting.
4. Reduced cost and labor in feature generation for predictive modeling. Curation of features via manual mapping between ICD codebases represents a significant proportion of a predictive modeling endeavor.

In summary, the present graph-based clinical concept mapping algorithm advantageously benefits clinical concept mapping product and service offerings based on the prediction of disease, change in patient therapy, patient therapy adherence, and patient treatment response. The application of this algorithm can be expected to expedite generation of other features to thereby reduce project turn-around time due to the lack of dependence on manual clinical coding.

An illustrative implementation of a SNOMED mapping algorithm uses a custom-built software package developed in the python and Pyspark programming languages. The package can be run from the command line and has five distinct pieces of functionality.
  a. Mapping: Takes information extracted from https://athena.odysseusinc.com on ICD-9, ICD-10 and SNOMED vocabulary concepts in Observational Medical Outcomes Partnership (OMOP) (Table 1, indicated by reference numeral 800 in FIG. 8), and ICD to SNOMED mapping relationships (Table 2, indicated by reference numeral 900 in FIG. 9) and produces a table with the structure shown in Table 3 (indicated by reference numeral 1000 in FIG. 10), whereby each row in Table 3 is a single ICD-9→SNOMED←ICD-10 link, and the table contains all combinations of such links.
  b. Pairing: Performs Orphan identification and pairing of ICD codes for a search paths in both directions, and keeps all resultant maps i.e. performs the search with query=ICD-9, target=ICD-10, then query=ICD-10, target=ICD-9, and keeps all identified mappings within a specified search radius (default is 5). This uses Table 3 (produced by the Mapping portion of code), and Table 4 (indicated by reference numeral 1100 in FIG. 11—defining the structure of the SNOMED graph) and produces a table of pairings from ICD-9→SNOMED→ICD-10 and ICD-10→SNOMED→ICD-9.
  c. Reduction: Reduces the identified mappings using one of the following options.
    i. No reduction (keep all pairs).
    ii. For each query, only keep pairs with the shortest distance between them on the SNOMED graph.
    iii. Select the semantically most similar concept using a Word2Vec algorithm.
  d. Post-processing: cleans up output mapping tables with additional information and has two modes.
    i. extract transform and load (ETL): produces a table of ICD→SNOMED mappings (for both ICD-10 and ICD-9) that can be used during ETL to convert ICD codes to SNOMED for medical claims data.
    ii. non-ETL: will add additional information (e.g. SNOMED, ICD full descriptions) to mappings table from reduction/pairing unnecessary for ETL processes.
  e. Rollup: can be used to roll up codes into higher-level, more prevalent aggregations based on the hierarchy of the code base used. Currently only used for rolling up SNOMED concepts after mapping ICD-9 and ICD-10 codes into SNOMED.

Figure 12:
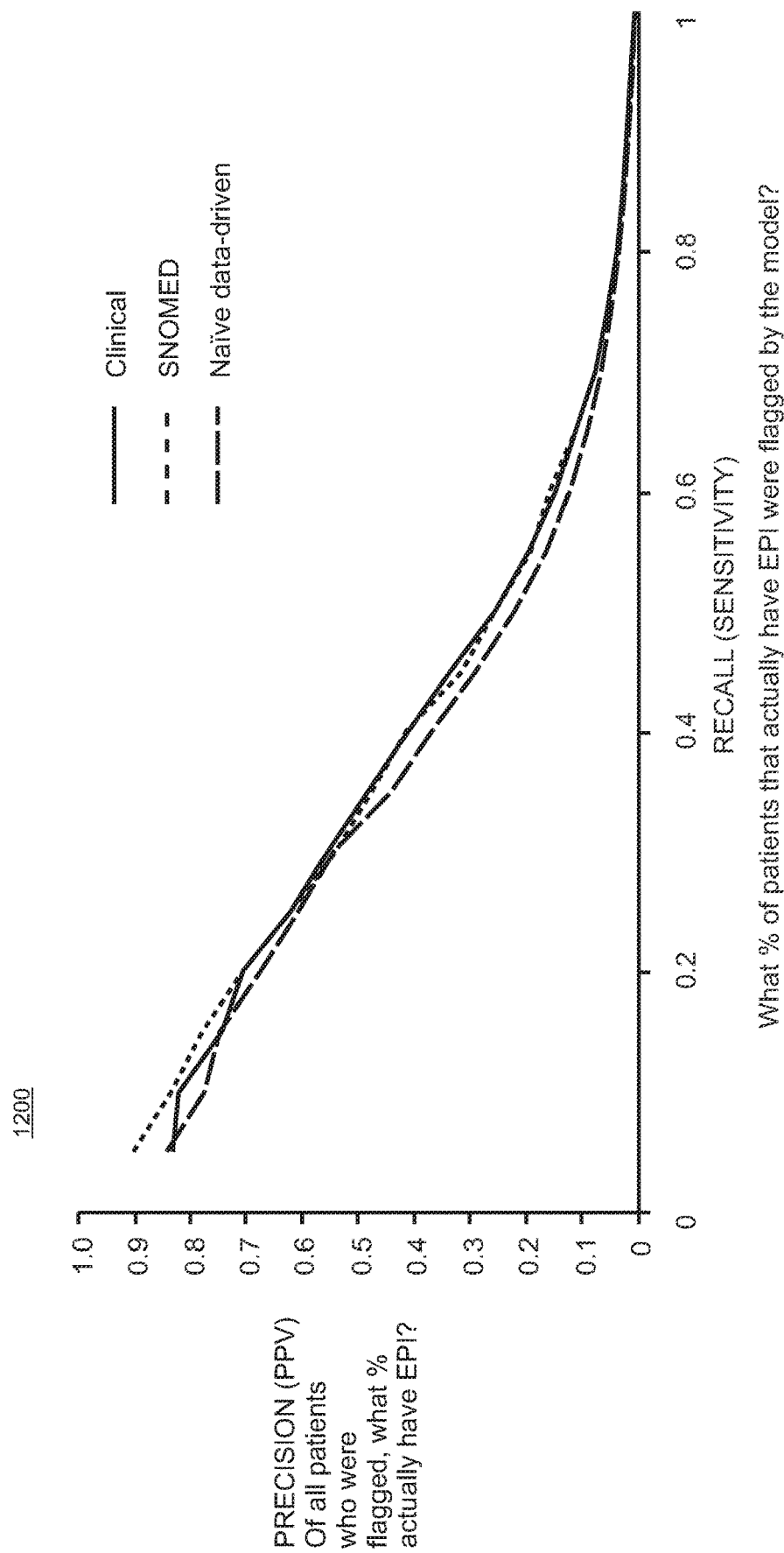
FIGS. 12 and 13 show respective illustrative precision-recall curves for two strategies for model evaluation.
Figure 13:
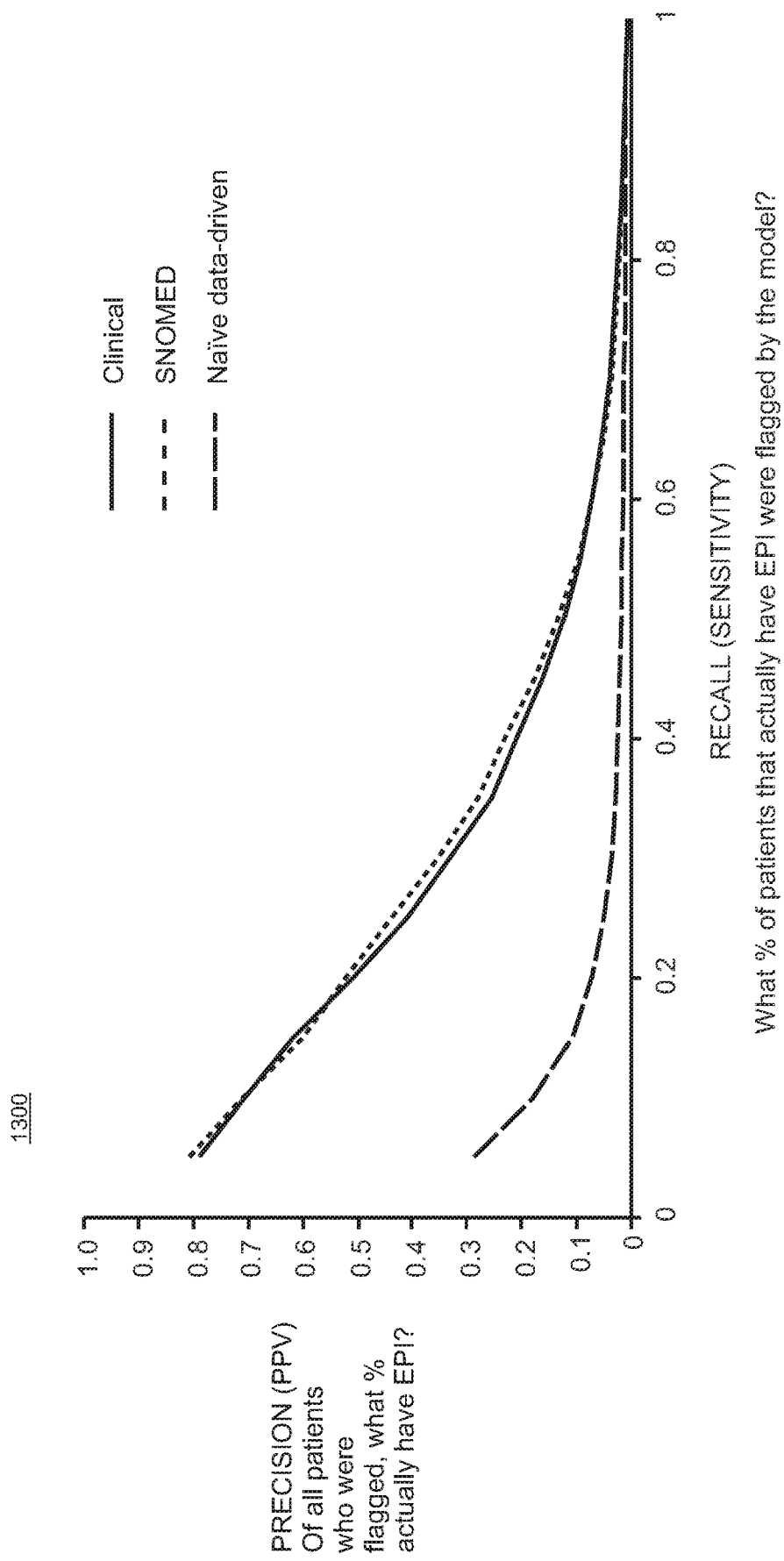

FIGS. 12 and 13 respectively show precision-recall curves 1200 and 1300 for strategies 1 and 2 discussed above. Models were trained using SNOMED (737), clinical expert (93) and naïve data driven (individual ICD concepts—715) features. For strategy 1, at 20% recall, precision was 71%, 71% and 68% for SNOMED, clinically driven and naïve data-driven respectively. For strategy 2, at 20% recall, precision was 51%, 51% and 7% for SNOMED, clinically driven and naïve data-driven respectively. With strategy 1, the model is trained on patients who have both data encoding using both ICD-9 and ICD-10. This allows the model to perform well on the validation data even on the naïve data-driven features as the validation patients also include both ICD versions. This is no longer the case for strategy 2, where the model is validated on patients whose medical history is exclusively encoded using ICD-10. Here, the value of the SNOMED based solution compared to the standard data-driven approach is clear. Successful mapping of ICD-9 and IDC-10 concepts allowed a model trained on ICD-9 information to extrapolate its predictions to patients in the ICD-10 space.

FIG. 14 is a flowchart of an illustrative method 1400 performed by a computing device to implement the present graph-based automated clinical concept mapping algorithm using SNOMED. Unless specifically stated, the methods or steps shown in the flowcharts and described in the accompanying text are not constrained to a particular order or sequence. In addition, some of the methods or steps thereof can occur or be performed concurrently and not all the methods or steps have to be performed in a given implementation depending on the requirements of such implementation and some methods or steps may be optionally utilized.

In step 1405, a SNOMED CT (Systematized Nomenclature of Medicine Clinical Terminology) ontology is organized in a directed acyclic graph (DAG) so that each of a plurality of diverse medical concepts is organized into respective nodes of the DAG. In step 1410, the ICD-9 codes and the ICD-10 codes are mapped to the SNOMED ontology as organized in the DAG. In step 1415, orphan ICD codes are identified, in which an orphan ICD code is one without an equivalent between ICD-9 and ICD-10 codebases. In step 1420, the DAG is traversed to establish unique ICD code and SNOMED pairings having shortest connecting paths on the DAG.

FIG. 15 is a flowchart of an illustrative alternative method 1500 performed by a computing device to implement the present graph-based clinical concept mapping algorithm. In step 1505, mappings between ICD (International Classification of Disease) codebases and a SNOMED CT ontology that is organized as a directed acyclic graph (DAG) are obtained, in which the ICD codebases are published as a series of revisions and at least include one previous revision and one subsequent revision. In step 1510, the mappings are used to identify orphan ICD codes without equivalents across the codebases. In step 1515, the DAG is traversed to pair the identified orphan ICD codes using codes from a previous ICD codebase revision as queries and codes from a subsequent ICD codebase revision as targets. In step 1520, the DAG traversal is repeated using codes from a subsequent ICD codebase revision as queries and codes from a previous ICD codebase revision as targets and the successive results of the pairings are merged. In step 1525, paired orphan ICD codes are reduced by removing duplicates or by keeping pairs that fall within a predetermined distance on the DAG. In an illustrative example, the previous ICD codebase revision is ICD-9 and the subsequent ICD codebase revision is ICD-10. In another illustrative example, at least one of the ICD codebases is ICD-X (i.e., ICD revision X), where X is a variable having an integer value (e.g., ICD-11, ICD-12 where is X is respectively equal to 11 and 12).

FIG. 16 is a flowchart of an illustrative alternative method 1600 performed by a computing device to implement the present graph-based clinical concept mapping algorithm. In step 1605, information is extracted from a database of ICD-9 (International Classification of Disease, Revision 9), ICD-10 (International Classification of Disease, Revision 10) and SNOMED (Systematized Nomenclature of Medicine) vocabulary concepts. In step 1610, mappings between ICD (International Classification of Disease) codebases and a SNOMED CT ontology are obtained that is represented as a directed acyclic graph (DAG). In step 1615, the extracted information and mappings are utilized to produce a mapping table in which each table entry comprises a single ICD-9→SNOMED←ICD-10 link and in which the mapping table comprises all combinations of ICD-9→SNOMED←ICD-10 links. In step 1620, ICD-9 and ICD-10 codes are paired using the mapping table and structure of the DAG to identify orphan codes and to produce a table of pairings of the orphan codes, wherein the pairings are produced from ICD-9→SNOMED→ICD-10 and from ICD-10→SNOMED→ICD-9.

Figure 17:
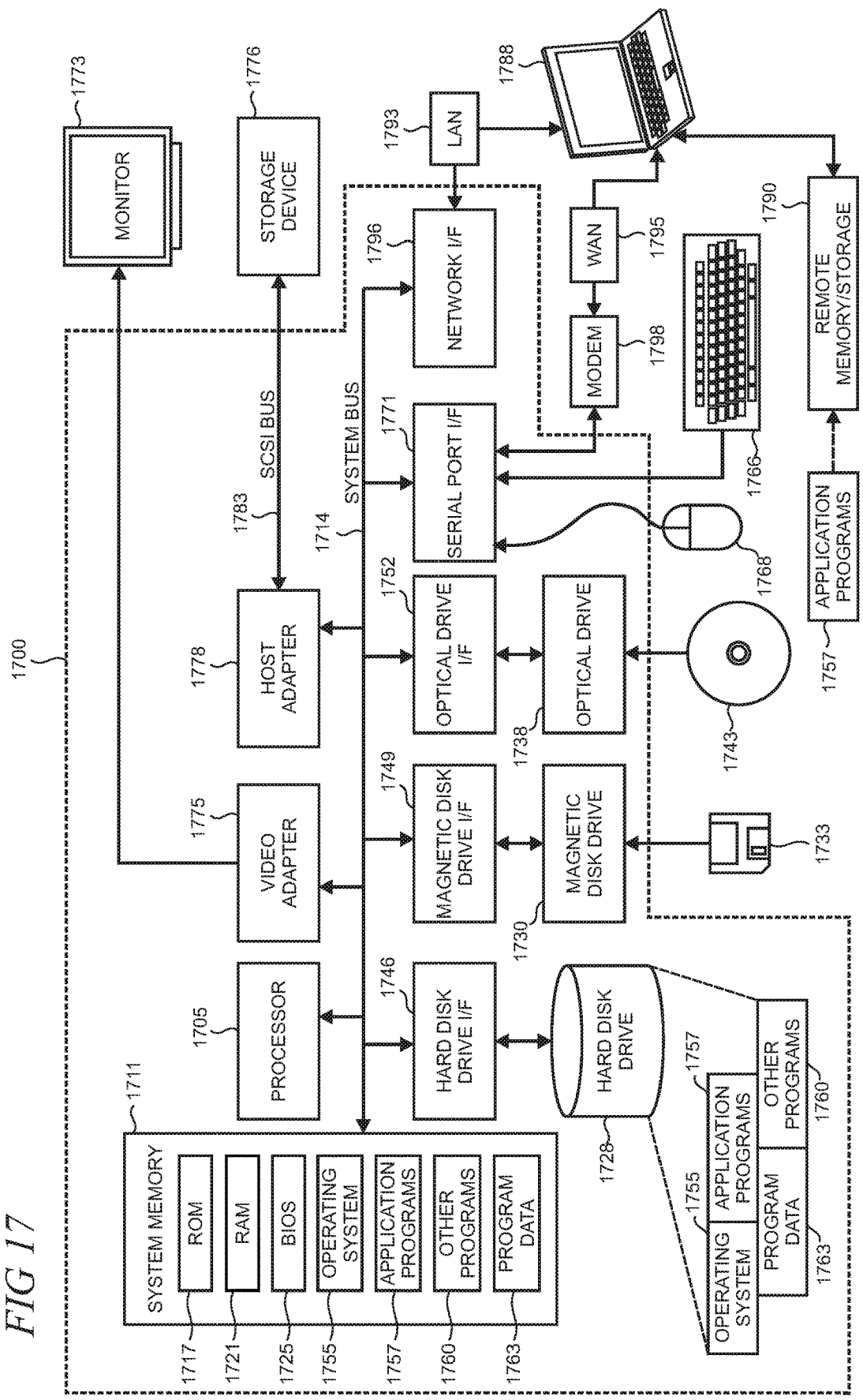
FIG. 17 is a block diagram of an illustrative architecture of a computing system such as a PC (personal computer) or server that may be used at least in part to implement the present graph-based clinical concept mapping algorithm.

FIG. 17 is a simplified block diagram of an illustrative architecture of a computer system 1700 such as a PC or server with which automated clinical concept mapping using SNOMED may be implemented. Computer system 1700 includes a processor 1705, a system memory 1711, and a system bus 1714 that couples various system components including the system memory 1711 to the processor 1705. The system bus 1714 may be any of several types of bus structures including a memory bus or memory controller, a peripheral bus, or a local bus using any of a variety of bus architectures. The system memory 1711 includes read only memory (ROM) 1717 and random-access memory (RAM) 1721. A basic input/output system (BIOS) 1725, containing the basic routines that help to transfer information between elements within the computer system 1700, such as during startup, is stored in ROM 1717. The computer system 1700 may further include a hard disk drive 1728 for reading from and writing to an internally disposed hard disk (not shown), a magnetic disk drive 1730 for reading from or writing to a removable magnetic disk 1733 (e.g., a floppy disk), and an optical disk drive 1738 for reading from or writing to a removable optical disk 1743 such as a CD (compact disc), DVD (digital versatile disc), or other optical media. The hard disk drive 1728, magnetic disk drive 1730, and optical disk drive 1738 are connected to the system bus 1714 by a hard disk drive interface 1746, a magnetic disk drive interface 1749, and an optical drive interface 1752, respectively. The drives and their associated computer-readable storage media provide non-volatile storage of computer-readable instructions, data structures, program modules, and other data for the computer system 1700. Although this illustrative example includes a hard disk, a removable magnetic disk 1733, and a removable optical disk 1743, other types of computer-readable storage media which can store data that is accessible by a computer such as magnetic cassettes, Flash memory cards, digital video disks, data cartridges, random access memories (RAMs), read only memories (ROMs), and the like may also be used in some applications of the present graph-based clinical concept mapping algorithm. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof, are intended to cover non-transitory embodiments, and do not include waves, signals, and/or other transitory and/or intangible communication media.

A number of program modules may be stored on the hard disk, magnetic disk 1733, optical disk 1743, ROM 1717, or RAM 1721, including an operating system 1755, one or more application programs 1757, other program modules 1760, and program data 1763. A user may enter commands and information into the computer system 1700 through input devices such as a keyboard 1766 and pointing device 1768 such as a mouse. Other input devices (not shown) may include a microphone, joystick, game pad, satellite dish, scanner, trackball, touchpad, touchscreen, touch-sensitive device, voice-command module or device, user motion or user gesture capture device, or the like. These and other input devices are often connected to the processor 1705 through a serial port interface 1771 that is coupled to the system bus 1714, but may be connected by other interfaces, such as a parallel port, game port, or universal serial bus (USB). A monitor 1773 or other type of display device is also connected to the system bus 1714 via an interface, such as a video adapter 1775. In addition to the monitor 1773, personal computers typically include other peripheral output devices (not shown), such as speakers and printers. The illustrative example shown in FIG. 17 also includes a host adapter 1778, a Small Computer System Interface (SCSI) bus 1783, and an external storage device 1776 connected to the SCSI bus 1783.

The computer system 1700 is operable in a networked environment using logical connections to one or more remote computers, such as a remote computer 1788. The remote computer 1788 may be selected as another personal computer, a server, a router, a network PC, a peer device, or other common network node, and typically includes many or all of the elements described above relative to the computer system 1700, although only a single representative remote memory/storage device 1790 is shown in FIG. 17. The logical connections depicted in FIG. 17 include a local area network (LAN) 1793 and a wide area network (WAN) 1795. Such networking environments are often deployed, for example, in offices, enterprise-wide computer networks, intranets, and the Internet.

When used in a LAN networking environment, the computer system 1700 is connected to the local area network 1793 through a network interface or adapter 1796. When used in a WAN networking environment, the computer system 1700 typically includes a broadband modem 1798, network gateway, or other means for establishing communications over the wide area network 1795, such as the Internet. The broadband modem 1798, which may be internal or external, is connected to the system bus 1714 via a serial port interface 1771. In a networked environment, program modules related to the computer system 1700, or portions thereof, may be stored in the remote memory storage device 1790. It is noted that the network connections shown in FIG. 17 are illustrative and other means of establishing a communications link between the computers may be used depending on the specific requirements of an application of the graph-based clinical concept mapping algorithm.

Figure 18:
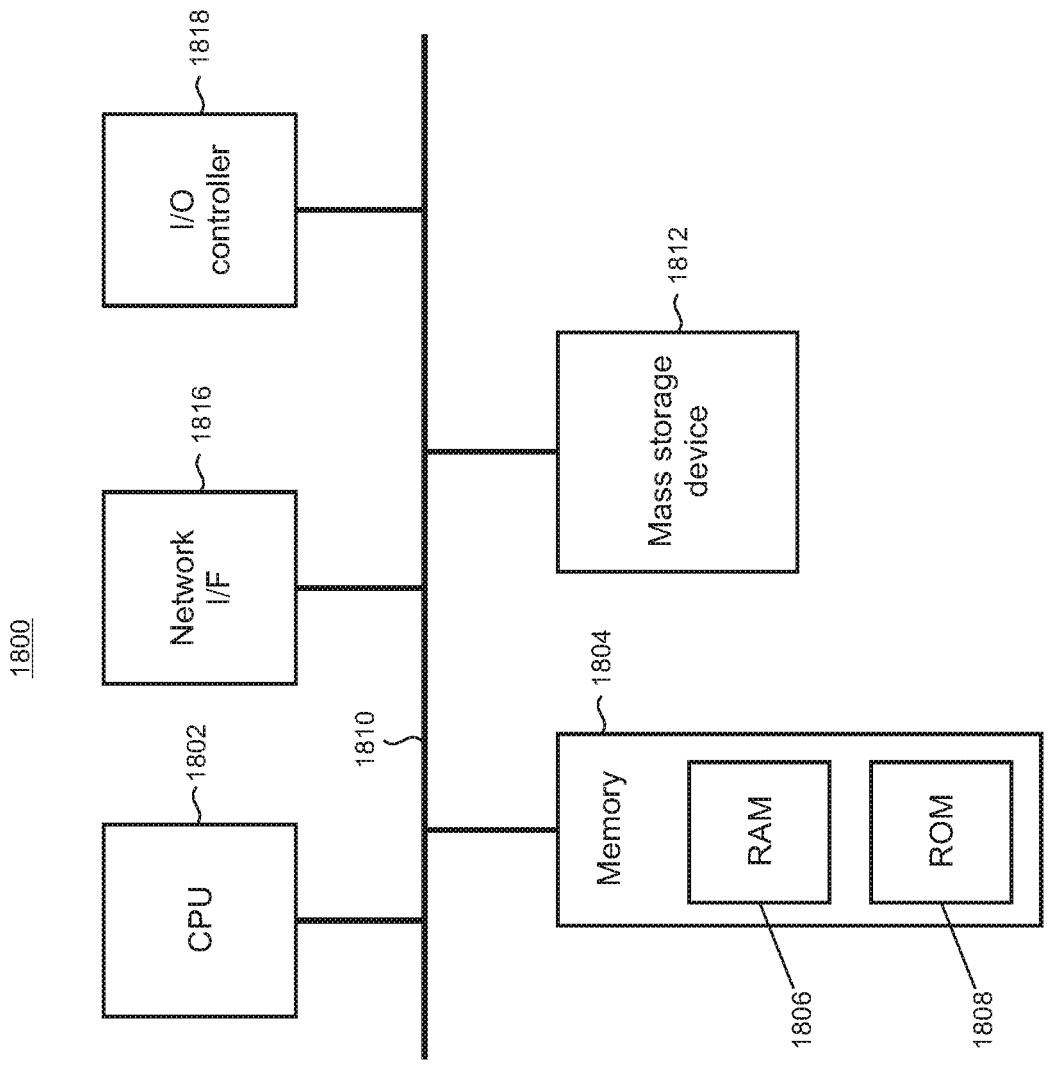
FIG. 18 is a simplified block diagram of an illustrative architecture of a computing device that may be used at least in part to implement the present graph-based clinical concept mapping algorithm.

FIG. 18 shows an illustrative architecture 1800 for a client computing device such as a laptop computer or personal computer for the present graph-based clinical concept mapping algorithm. The architecture 1800 illustrated in FIG. 18 includes one or more processors 1802 (e.g., central processing unit, dedicated Artificial Intelligence chip, graphics processing unit, etc.), a system memory 1804, including RAM (random access memory) 1806 and ROM (read only memory) 1808, and a system bus 1810 that operatively and functionally couples the components in the architecture 1800. A basic input/output system containing the basic routines that help to transfer information between elements within the architecture 1800, such as during startup, is typically stored in the ROM 1808. The architecture 1800 further includes a mass storage device 1812 for storing software code or other computer-executed code that is utilized to implement applications, the file system, and the operating system. The mass storage device 1812 is connected to the processor 1802 through a mass storage controller (not shown) connected to the bus 1810. The mass storage device 1812 and its associated computer-readable storage media provide non-volatile storage for the architecture 1800. Although the description of computer-readable storage media contained herein refers to a mass storage device, such as a hard disk or CD-ROM drive, it may be appreciated by those skilled in the art that computer-readable storage media can be any available storage media that can be accessed by the architecture 1800.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read only memory), EEPROM (electrically erasable programmable read only memory), Flash memory or other solid state memory technology, CD-ROM, DVD, HD-DVD (High Definition DVD), Blu-ray or other optical storage, magnetic cassette, magnetic tape, magnetic disk storage or other magnetic storage device, or any other medium which can be used to store the desired information and which can be accessed by the architecture 1800.

According to various embodiments, the architecture 1800 may operate in a networked environment using logical connections to remote computers through a network. The architecture 1800 may connect to the network through a network interface unit 1816 connected to the bus 1810. It may be appreciated that the network interface unit 1816 also may be utilized to connect to other types of networks and remote computer systems. The architecture 1800 also may include an input/output controller 1818 for receiving and processing input from a number of other devices, including a keyboard, mouse, touchpad, touchscreen, control devices such as buttons and switches or electronic stylus (not shown in FIG. 18). Similarly, the input/output controller 1818 may provide output to a display screen, user interface, a printer, or other type of output device (also not shown in FIG. 18).

It may be appreciated that the software components described herein may, when loaded into the processor 1802 and executed, transform the processor 1802 and the overall architecture 1800 from a general-purpose computing system into a special-purpose computing system customized to facilitate the functionality presented herein. The processor 1802 may be constructed from any number of transistors or other discrete circuit elements, which may individually or collectively assume any number of states. More specifically, the processor 1802 may operate as a finite-state machine, in response to executable instructions contained within the software modules disclosed herein. These computer-executable instructions may transform the processor 1802 by specifying how the processor 1802 transitions between states, thereby transforming the transistors or other discrete hardware elements constituting the processor 1802.

Encoding the software modules presented herein also may transform the physical structure of the computer-readable storage media presented herein. The specific transformation of physical structure may depend on various factors in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

In light of the above, it may be appreciated that many types of physical transformations take place in the architecture 1800 in order to store and execute the software components presented herein. It also may be appreciated that the architecture 1800 may include other types of computing devices, including wearable devices, handheld computers, embedded computer systems, smartphones, PDAs, and other types of computing devices known to those skilled in the art. It is also contemplated that the architecture 1800 may not include all of the components shown in FIG. 18, may include other components that are not explicitly shown in FIG. 18, or may utilize an architecture completely different from that shown in FIG. 18.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computing device comprising:
   one or more processors; and
   one or more hardware-based computer-readable memory devices storing instructions which, when executed by the one or more processors, cause the computing device to:
   map codes of a first International Classification of Disease (ICD) codebase and codes of a second ICD codebase to Systematized Nomenclature of Medicine Clinical Terminology (SNOMED CT) concepts by obtaining and using external SNOMED CT mappings;

generate a directed acyclic graph (DAG) of the SNOMED CT concepts comprising the codes of the first and second ICD codebases mapped thereon:

identify one or more codes of the first ICD codebase and one or more codes of the second ICD codebase unpaired with a shared SNOMED CT concept on the DAG;

identify, for each of the unpaired codes of the first ICD codebase and the second ICD codebase, a common SNOMED CT concept on the DAG;

determine, for each of the unpaired codes of the first ICD codebase and the second ICD codebase having a common SNOMED CT concept, a semantic similarity of clinical descriptions therebetween; and pair one or more of the identified unpaired codes of the first ICD codebase and one or more of the identified unpaired codes of the second ICD codebase based on their respective common SNOMED CT concept and their respective semantic similarity.

2. The computing device of claim 1 in which the instructions further cause the computing device to utilize a neural network to identify pairs of the codes of the first and second ICD codebases according to semantic similarity of clinical descriptions, wherein the codes of the first ICD codebase include 5 characters and the codes of the second ICD codebase include 7 characters.

3. The computing device of claim 1 in which the instructions further cause the computing device to obtain the ICD code to SNOMED mappings from an external system.

4. The computing device of claim 3 in which the external system provides Observational Medical Outcomes Partnership (OMOP) ICD to SNOMED mapping data for the first and second ICD codebases and provides the SNOMED directed acyclic graph (DAG) data.

5. The computing device of claim 1 in which the instructions further cause the computing device to produce mappings of the codes of the first and second ICD codebases to SNOMED concepts whereby multiple ICD codes are rolled up into a single SNOMED concept.

6. The computing device of claim 5 in which the instructions further cause the computing device to rollup the SNOMED concepts using the directed acyclic graph (DAG).

7. The computing device of claim 6 in which the rollup comprises rolling up each ICD code that is below a predetermined threshold until each ICD code is aggregated in a SNOMED concept that is above the predetermined threshold.

8. The computing device of claim 7 in which the instructions further cause the computing device to delete rolled-up SNOMED codes.

9. The computing device of claim 8 in which the instructions further cause the computing device to keep redundant rolled-up SNOMED codes.

10. The computing device of claim 1, wherein the first ICD codebase is International Classification of Disease, Revision 9 (ICD-9) and the second ICD codebase is International Classification of Disease, Revision 10 (ICD-10), and the clinical descriptions of the ICD-10 codes semantically match the clinical descriptions of the respective ICD-9 codes.

11. The computing device of claim 1, wherein identifying the one or more codes of the second ICD codebase comprises searching a predetermined number of the codes of the second ICD codebase.

12. The computing device of claim 1, wherein identifying one or more codes of the second ICD codebase having clinical descriptions semantically similar to the respective code of the first ICD codebase comprises identifying the one or more codes of the second ICD codebase having a cosine similarity to the respective code of the first ICD codebase.

13. The device of claim 1, wherein each of the unpaired one or more codes of the first ICD codebase is mapped to a SNOMED CT concept lacking a corresponding mapped code of the second ICD codebase, and wherein each of the unpaired one or more codes of the second ICD codebase is mapped to a SNOMED CT concept lacking a corresponding mapped code of the first ICD codebase.

14. A method for automated clinical concept mapping using SNOMED CT (Systematized Nomenclature of Medicine Clinical Terms), comprising:

obtaining mappings between ICD (International Classification of Disease) codebases and a SNOMED CT ontology that is organized as a directed acyclic graph (DAG), and using the mappings to map codes of a first ICD codebase and codes of a second ICD codebase to SNOMED CT concepts on the DAG;

identifying one or more of the codes of the fist ICD codebase and the second ICD codebase unpaired with a shared SNOMED CT concept on the DAG;

identifying, for each of the unpaired codes of the first ICD codebase and the second ICD codebase, a common SNOMED CT concept on the DAG;

determining, for each of the unpaired codes of the first ICD codebase and the second ICD codebase having a common SNOMED CT concept, a semantic similarity of clinical descriptions therebetween; and pairing one or more of the identified unpaired codes of the first ICD codebase and one or more of the identified unpaired codes of the second ICD codebase based on their respective common SNOMED CT concept and their respective semantic similarity.

15. The method of claim 14 in which the pairing of codes comprises for queries, identifying all ancestors in the DAG as pivot nodes, for all target nodes, identifying all possible ancestors, identifying target node ancestors that are pivots to queries such that queries are linked to targets by the pivot nodes, and utilizing search paths by linking to pivots having lower positions in the DAG.

16. The method of claim 15 in which the identified ancestors for the target nodes include ancestors that are within a predetermined minimum separation distance on the DAG.

17. The method of claim 14 in which each of the first and second ICD codebases include one of ICD-9 (International Classification of Disease, Revision 9), ICD-10 (International Classification of Disease, Revision 10) or ICD-X (International Classification of Disease, Revision 10) in which X is a variable having an integer value.

18. One or more computer-readable media storing instructions which, when executed by one or more processors in a computing device cause the computing device to:

obtain mappings between ICD (International Classification of Disease) codebases and a Systematized Nomenclature of Medicine Clinical Terminology (SNOMED CT) ontology that is represented as a directed acyclic graph (DAG), and using the mappings to map codes of a first ICD codebase and codes of a second ICD codebase to SNOMED CT concepts on the DAG;

identify one or more of the codes of the first ICD codebase and the second ICD codebase unpaired with a shared SNOMED CT concept on the DAG;

identify, for each of the unpaired codes of the first ICD codebase and the second ICD codebase, a common SNOMED CT concept on the DAG;

determine, for each of the identified one or more unpaired codes of the first ICD codebase and the second ICD codebase having a common SNOMED CT concept, a semantic similarity of clinical descriptions therebetween; and pair one or more of the identified unpaired codes of the fist ICD codebase and one or more of the identified unpaired codes of the second ICD codebase based on their respective common SNOMED CT concept and their respective semantic similarity.

19. The one or more computer-readable media of claim 18 in which vocabulary concepts are provided by an Observational Medical Outcomes Partnership (OMOP).

20. The one or more computer-readable media of claim 18 in which the first ICD codebase is International Classification of Disease, Revision 9 (ICD-9) and the second ICD codebase is International Classification of Disease, Revision 10 (ICD-10), and the instructions further cause the computing device to search for pairings in both directions using query=ICD-9, target=ICD-10 and query=ICD-10, target=ICD-9.

21. The one or more computer-readable media of claim 20 in which the instructions further cause the computing device to keep pairings that are within a predetermined radius on the DAG.

22. The one or more computer-readable media of claim 18 in which the instructions further cause the computing device to reduce entries in a table of pairings by keeping pairings having a shortest distance on the DAG or by keeping pairings that are determined to be semantically similar.

23. The one or more computer-readable media of claim 18, wherein the codes of the second ICD codebase are a predetermined number of nodes within a fixed search radius.

24. The one or more computer-readable media of claim 23 in which the instructions further cause the computing device to produce an output table of ICD code pairs that supports one of ETL (extract, transform, and load) functionality by including ICD→SNOMED mappings for both the first and second ICD codebases that are usable during ETL to convert the ICD codes to SNOMED, or non-ETL functionality.

* * * * *